United States Patent
Paunescu et al.

(10) Patent No.: US 12,030,076 B2
(45) Date of Patent: Jul. 9, 2024

(54) UNIT DOSE ASEPTIC AEROSOL MISTING DEVICE

(71) Applicant: JOHNSON & JOHNSON CONSUMER INC., Skillman, NJ (US)

(72) Inventors: Alexandru Paunescu, Clinton, NJ (US); Richard J. Fougere, Washington Crossing, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 18/156,832

(22) Filed: Jan. 19, 2023

(65) Prior Publication Data
US 2023/0149966 A1   May 18, 2023

Related U.S. Application Data

(62) Division of application No. 15/337,417, filed on Oct. 28, 2016, now Pat. No. 11,583,885.
(Continued)

(51) Int. Cl.
| B05B 17/06 | (2006.01) |
| A61M 11/00 | (2006.01) |
| A61M 15/00 | (2006.01) |

(52) U.S. Cl.
CPC ......... B05B 17/063 (2013.01); A61M 11/005 (2013.01); A61M 15/0085 (2013.01);
(Continued)

(58) Field of Classification Search
CPC ............ A61M 15/0005; A61M 15/001; A61M 15/0028; A61M 15/0045; A61M 15/0048;
(Continued)

(56) References Cited

U.S. PATENT DOCUMENTS

| 3,812,854 A | 5/1974 | Michaels et al. |
| 4,004,736 A | 1/1977 | George |

(Continued)

FOREIGN PATENT DOCUMENTS

| BE | 1013167 A | 10/2001 |
| CA | 2082499 A | 11/1991 |

(Continued)

OTHER PUBLICATIONS

International Search Report, PCT Application No. PCT/US2016/059274, dated Feb. 3, 2017.

*Primary Examiner* — Qingzhang Zhou
*Assistant Examiner* — Juan C Barrera (57) ABSTRACT

A unit dose capsule for use with a sonic generator includes a deformable membrane adapted to releasably engage the distal end of the elongate horn, a nozzle including at least one delivery opening; a nozzle including at least one delivery opening; and a reservoir containing a liquid composition disposed therebetween. When the unit dose capsule is engaged to the distal end of the elongate horn, the nozzle is disposed in an outwardly facing orientation, and the reservoir is in liquid communication with the at least one nozzle. The unit dose capsule can be included in a kit with a handheld misting device comprising a housing having a dispensing window arranged and configured to contain a sonic generator and a power source.

4 Claims, 8 Drawing Sheets

Related U.S. Application Data (60) Provisional application No. 62/248,736, filed on Oct. 30, 2015.

(52) U.S. Cl.
CPC ..... *B05B 17/0676* (2013.01); *A61M 15/0021* (2014.02); *A61M 15/0048* (2014.02)

(58) Field of Classification Search
CPC .......... A61M 15/0085; A61M 15/0021; A61M 11/005; A61M 11/042; A61M 15/0051; A61M 11/001; A61M 2205/8206; A61M 15/0031; A61M 2205/12; A61M 15/06; A61M 11/00; A61M 11/007; A61M 15/0041; B05B 17/063; B05B 17/0676; B05B 17/0623; B05B 17/0607; A01M 1/205
USPC .............. 128/200.16, 200.17, 200.14; 239/4
See application file for complete search history.

(56) References Cited

U.S. PATENT DOCUMENTS

| | | | |
|---|---|---|---|
| 4,085,893 | A | 4/1978 | Durley, III |
| 4,301,968 | A | 11/1981 | Berger et al. |
| 4,696,719 | A | 9/1987 | Bischoff |
| 4,877,989 | A | 10/1989 | Drews et al. |
| 5,104,042 | A | 4/1992 | McKown |
| 5,166,000 | A | 11/1992 | Singh et al. |
| 5,307,640 | A | 5/1994 | Fawzy et al. |
| 5,515,842 | A | 5/1996 | Ramseyer et al. |
| 5,558,085 | A | 9/1996 | Rubsamen et al. |
| 5,632,445 | A | 5/1997 | Dubruque |
| 5,957,124 | A | 9/1999 | Lloyd et al. |
| 6,478,754 | B1 | 11/2002 | Babaev |
| 6,521,067 | B1 | 2/2003 | Clark |
| 6,601,581 | B1 | 8/2003 | Babaev |
| 6,669,103 | B2 | 12/2003 | Tsai |
| 6,748,944 | B1 | 6/2004 | DellaVecchia et al. |
| 6,837,445 | B1 | 1/2005 | Tsai |
| 6,863,224 | B2 | 3/2005 | Terada et al. |
| 6,901,926 | B2 | 6/2005 | Yamamoto et al. |
| 7,261,102 | B2 | 8/2007 | Barney et al. |
| 7,550,897 | B2 | 6/2009 | Hailes |
| 7,679,262 | B2 | 3/2010 | Meng et al. |
| 7,878,991 | B2 | 2/2011 | Babaev |
| 7,896,539 | B2 | 3/2011 | Babaev |
| 7,976,135 | B2 | 7/2011 | Brown et al. |
| 7,977,849 | B2 | 7/2011 | Hailes et al. |
| 7,992,800 | B2 | 8/2011 | Hsieh et al. |
| 8,016,209 | B2 | 9/2011 | Hess et al. |
| 8,061,629 | B2 | 11/2011 | Tranchant et al. |
| 8,123,502 | B2 | 2/2012 | Blakey et al. |
| 8,162,628 | B2 | 4/2012 | Meng et al. |
| 8,191,982 | B2 | 6/2012 | Brown et al. |
| 8,286,629 | B2 | 10/2012 | Esaki et al. |
| 8,297,947 | B2 | 10/2012 | Van Rensburg et al. |
| 8,317,299 | B2 | 11/2012 | Brown |
| 8,430,338 | B2 | 4/2013 | Duru et al. |
| 8,434,473 | B2 | 5/2013 | Tsai et al. |
| 8,684,980 | B2 * | 4/2014 | Hunter ................ B05B 17/0646 604/296 |
| 8,720,434 | B2 | 5/2014 | Imai |
| 8,763,606 | B2 * | 7/2014 | Mosier ................ A61M 15/005 128/203.15 |
| 8,821,802 | B2 | 9/2014 | Haran |
| 8,944,344 | B2 | 2/2015 | Donaty |
| 8,961,496 | B2 | 2/2015 | Locke et al. |
| 9,067,427 | B2 | 6/2015 | Hayashi |
| 9,068,566 | B2 | 6/2015 | Ivri |
| 9,168,555 | B2 | 10/2015 | Tsai |
| 9,549,753 | B2 | 1/2017 | Gordon |
| 9,565,870 | B2 | 2/2017 | Deo et al. |
| 2003/0199083 | A1 | 10/2003 | Vilendrer et al. |
| 2003/0234298 | A1 | 12/2003 | Cher |
| 2004/0045547 | A1 | 3/2004 | Yamamoto |
| 2004/0123864 | A1 | 7/2004 | Hickey et al. |
| 2004/0188546 | A1* | 9/2004 | Tabata ................... B05B 11/02 239/436 |
| 2006/0113496 | A1 | 6/2006 | Yoshioka |
| 2006/0196518 | A1 | 9/2006 | Hon |
| 2006/0243277 | A1 | 11/2006 | Denyer et al. |
| 2007/0189919 | A1 | 8/2007 | Prince et al. |
| 2007/0240706 | A1 | 10/2007 | Kobayashi et al. |
| 2008/0051693 | A1 | 2/2008 | Babaev |
| 2009/0065600 | A1 | 3/2009 | Tranchant et al. |
| 2009/0133691 | A1 | 5/2009 | Yamada et al. |
| 2009/0223513 | A1 | 9/2009 | Papania et al. |
| 2009/0314853 | A1 | 12/2009 | Feriani et al. |
| 2010/0068080 | A1 | 3/2010 | Meng et al. |
| 2010/0072299 | A1 | 3/2010 | Hsieh et al. |
| 2010/0147292 | A1 | 6/2010 | Hamaguchi et al. |
| 2010/0206307 | A1 | 8/2010 | Imai |
| 2011/0268605 | A1 | 11/2011 | Haran |
| 2011/0277491 | A1 | 11/2011 | Wu et al. |
| 2011/0290241 | A1 | 12/2011 | Maeda et al. |
| 2012/0179122 | A1 | 7/2012 | Eilat et al. |
| 2012/0205468 | A1 | 8/2012 | Hsieh et al. |
| 2012/0279533 | A1 | 11/2012 | Kato et al. |
| 2012/0285446 | A1* | 11/2012 | Van Der Mark .... A61M 11/005 128/200.14 |
| 2012/0302979 | A1 | 11/2012 | Locke et al. |
| 2012/0304929 | A1 | 12/2012 | Ivri |
| 2012/0318260 | A1 | 12/2012 | Hsieh et al. |
| 2013/0108748 | A1 | 5/2013 | Deo et al. |
| 2013/0129392 | A1 | 5/2013 | Wakabayashi et al. |
| 2013/0307911 | A1 | 11/2013 | Hayashi |
| 2013/0319404 | A1 | 12/2013 | Feriani et al. |
| 2014/0184095 | A1 | 7/2014 | Yoshinaga et al. |
| 2014/0231538 | A1 | 8/2014 | Tabata et al. |
| 2015/0014433 | A1 | 1/2015 | Albert et al. |
| 2015/0014434 | A1 | 1/2015 | Fedorov |
| 2017/0120284 | A1 | 5/2017 | Paunescu et al. |
| 2017/0120285 | A1 | 5/2017 | Paunescu et al. |
| 2017/0128971 | A1 | 5/2017 | Paunescu et al. |
| 2017/0128972 | A1 | 5/2017 | Paunescu |
| 2019/0329280 | A1 | 10/2019 | Paunescu |

FOREIGN PATENT DOCUMENTS

| | | |
|---|---|---|
| CN | 101773894 A | 7/2010 |
| CN | 204951864 U | 1/2016 |
| EP | 82896 B | 3/1986 |
| EP | 416106 A | 3/1991 |
| EP | 615470 A | 9/1994 |
| EP | 1092541 A | 4/2001 |
| EP | 2413030 A | 2/2012 |
| GB | 807080 A | 1/1959 |
| GB | 2099710 A | 12/1982 |
| JP | S57200229 U | 12/1982 |
| JP | 61057258 A | 2/1986 |
| JP | 61141955 A | 6/1986 |
| JP | 63049271 A | 3/1988 |
| JP | 4267964 A | 9/1992 |
| JP | 5161705 A | 6/1993 |
| JP | 1993095673 U | 12/1993 |
| JP | 8332425 A | 12/1996 |
| JP | 9173925 A | 7/1997 |
| JP | 10005711 A | 1/1998 |
| JP | 2001149473 A | 6/2001 |
| JP | 2003251239 A | 9/2003 |
| JP | 2010142737 A | 7/2010 |
| JP | 2012130903 A | 7/2012 |
| WO | WO 1993/010910 A | 6/1993 |
| WO | WO 1996/009846 A | 4/1996 |
| WO | WO 2006/006963 A | 1/2006 |
| WO | WO 2008/097645 A | 8/2008 |
| WO | WO 2011/083380 A | 7/2011 |
| WO | WO 2014/165694 A | 10/2014 |
| WO | WO 2014/184095 A | 11/2014 |

\* cited by examiner

UNIT DOSE ASEPTIC AEROSOL MISTING DEVICE

CROSS-REFERENCE TO RELATED APPLICATION

This application is a divisional of U.S. application Ser. No. 15/337,417 filed Oct. 28, 2016, which claims the benefit of U.S. provisional application 62/248,736, filed Oct. 30, 2015, the complete disclosures of which are hereby incorporated herein by reference for all purposes.

FIELD OF THE INVENTION

The present invention relates to a unit dose aseptic misting device employing a permanent sonic generator and a replaceable liquid reservoir and nozzle.

BACKGROUND OF THE INVENTION

Spray and/or misting devices are often used to deliver cosmetic and general health care liquids. Low cost systems employ droppers and/or squeeze bottles with some form of nozzle through which the liquid is forced to provide a relatively uncontrolled dosage and droplet size.

Expensive systems may employ metering pumps and/or expensive aerosol forming components. For example, Hseih et al. U.S. Pat. No. 7,992,800 and Hseih et al. U.S. Pub. Pat. Appn. No. 20120318260 disclose nebulizers driven by piezo-electric and/or magnetic drives to generate an aerosol mist.

Other examples include The Technology Partnership PLC, EP615470B1; Hailes et al., U.S. Pat. No. 7,550,897, and Brown et al. U.S. Pat. No. 7,976,135, which disclose liquid projection apparatus employing transducers to project liquid droplets from an outer face of a nozzle.

Finally, Terada et al. U.S. Pat. No. 6,863,224, Yamamoto et al. U.S. Pat. No. 6,901,926, and Esaki et al. U.S. Pat. No. 8,286,629 disclose ultrasonic liquid atomizing devices. Unfortunately, these expensive components can be contaminated through repeated uses and require careful cleaning or disposal.

What is needed is a relatively low cost system for delivering controlled individual or unit doses and particle/droplet size aerosol mists.

SUMMARY OF THE INVENTION

Surprisingly, we have found that ultrasonically atomizing a liquid through submillimeter-sized nozzles using a deformable membrane maintains the integrity of the membrane throughout the use to enable aseptic atomization by preventing the liquid encapsulated in the reservoir-membrane assembly from touching the ultrasonic horn.

In one aspect of the invention, a unit dose capsule for use with a sonic generator includes a deformable membrane adapted to releasably engage the distal end of the elongate horn; a nozzle including at least one delivery opening; and a reservoir containing a liquid composition disposed therebetween. When the unit dose capsule is engaged to the distal end of the elongate horn, the nozzle is disposed in an outwardly facing orientation, and the reservoir is in liquid communication with the at least one nozzle.

In another aspect of the invention, the unit dose capsule is included in a kit with a handheld misting device comprising a housing having a dispensing window arranged and configured to contain a sonic generator and a power source coupled to the sonic generator. The sonic generator includes a converter and an elongate horn having a proximal end coupled to the converter and a distal end arranged and configured to transmit sonic energy outside of the housing.

In another aspect of the invention, a method of generating an aerosol mist includes coupling a first unit dose capsule to the handheld misting device, energizing the device to generate an aerosol mist, removing the first unit dose capsule from the distal end of the elongate horn, coupling a second unit dose capsule to the distal end of the elongate horn; and energizing the sonic generator to generate an aerosol mist. Each unit dose capsule is coupled to the distal end of the elongate horn, each unit dose capsule includes a deformable membrane adapted to releasably engage the distal end of the elongate horn, a nozzle including at least one delivery opening; a nozzle including at least one delivery opening; and a reservoir containing a liquid composition disposed therebetween. The step of energizing the sonic generator includes engaging the distal end of the elongate horn with the deformable membrane, and transmitting sonic energy through the deformable membrane to the liquid composition.

DETAILED DESCRIPTION OF THE PREFERRED EMBODIMENTS

The present invention relates to a handheld sonic misting device that is more economical than conventional sonic misting devices, because the relatively expensive sonic generator and horn are isolated from unit dosage liquids dispensed by the misting device. Thus, the misting device can be replenished with liquids without any build-up of liquids on the horn.

In one form of the device, shown in FIGS. 1-4, the handheld misting device 100 includes a housing 200 containing a sonic generator 300 and an electric power and control system 400. The handheld misting device 100 can be used with a series of unit dose capsules 500.

As shown in FIG. 1, the housing 200 includes an elongate, generally cylindrical outer sleeve 202 having a back end 204 and a front end 206. The outer sleeve 202 has a generally uniform cross section from the back end 204 extending towards the front end 206 that contains the electric power and control system 400 and the converter 302 of the sonic generator 300. A front portion 208 of the outer sleeve 202 tapers towards a receptacle 210 having a dispensing window 211 arranged and configured to accommodate a unit dose capsule 500. An elongate horn 304 extends from the sonic converter 302 toward the front end 206 of the housing 200.

The electric power and control system 400 includes a power source, such as a battery 402, one or more control boards 404.

In the embodiment of FIGS. 1-4, the housing 200 includes an inner sleeve 212 that is slidable within the outer sleeve 202. The back end 214 of the inner sleeve 212 protrudes outwardly beyond the back end 204 of the outer sleeve 202, and the inner sleeve 212 provides a frame on which the battery 402, control board 404, and sonic generator 300 are secured. A spring 216 is disposed between the sonic converter 302 and the front end 206 of the outer sleeve 202. This spring 216 provides resistance to movement of the inner sleeve 212 towards the front end 206 of the outer sleeve 202 except when desired to activate the device.

One example of a unit dose capsule 500 is shown in FIGS. 5-7. The unit dose capsule 500 is cylindrical reservoir with a thickness less than a diameter. The reservoir has a first substantially planar surface 502 having at least one delivery opening 504 through which the liquid 310 contained therein can be dispensed in the form of the aerosol mist, described generally above. The opposite substantially planar surface 506 of the reservoir is in the form of a thin membrane 508 anchored in the walls 510 of the reservoir, e.g., in slot 512.

The delivery opening(s) 504 are dimensioned to deliver an aerosol mist. Preferably, each delivery opening has a maximum dimension (across the opening) of less than about 200 microns (μm), more preferably, between about 50 and about 150 μm. Preferred delivery openings are generally circular, but one of ordinary skill in the art may modify this to achieve specifically desired aerosol properties. The number of delivery openings is selected to deliver a desired misting flow. Capsules with one delivery opening have been shown to produce a useful aerosol plume, and other capsules with 6 and 7 openings have also produced useful aerosol plumes. Therefore, one of ordinary skill in the art may select from one to more than ten delivery openings. The delivery openings may have a constant channel (as shown in FIG. 6, or they may vary from the reservoir surface to the exterior surface of the unit dose capsule. Tapering or other funneling of the side walls can help to control the aerosol plume. Examples of such forms are shown in FIG. 8A (tapered, or fruso-conical), 8B, ("Y-shaped", having a fruso-conical first section 504*a* and a constant channel second section 504*b*), and 8C (having a hemispherical first section 504*a'* and a constant channel second section 504*b*.

In use, an operator may turn activate the power switch 406 to energize the sonic generator 300, hold the outer sleeve 202 of the housing 200 (e.g., between a thumb and one or more fingers), and use another finger to press on the back end 214 of the inner sleeve 212 to urge the inner sleeve 212 toward the front end 206 of the outer sleeve 202 to overcome the resistance of the spring 216. As shown in FIGS. 9 and 10, this movement (indicated by arrow 218) forces the distal end 306 of the elongate horn 304 to directly engage the membrane 508 of the unit dose capsule 500 and to drive the liquid 310 through the delivery opening(s) 504, thereby generating the aerosol mist 308. The size, shape, number, and arrangement of delivery opening(s) 504 define the plume of mist 308 generated by the misting device 100.

The present invention is useful in the delivery of aerosol plumes of medication and/or moisturizing solutions in a more sanitary manner than currently provided. Sonic generation of aerosol plumes can provide very fine mists, having a droplet size between about 20 and about 60 μm, given by the practical range of frequencies for the ultrasonic horn between 20 kHz and 200 kHz.

In an alternative embodiment, a plurality of unit dose capsules can be incorporated into a revolver. In FIGS. 11A-C, a four-unit dose revolver 600 is shown. As shown in FIG. 11A, a circular revolver 600 includes four unit dose capsules 602. Each capsule 602 has a membrane 604 disposed on the side facing the horn, and a removable, protective tab 606 covering the delivery openings (not shown) on the exterior side. This tab 606 may be removed by the user, or automatically via a scraper (not shown). The revolver 600 is rotatable about axle 608, and it may be indexed to align with the horn through a mechanical linkage, or through a solenoid-controlled rotator (not shown).

In a further alternative embodiment, shown in FIGS. 12 and 13, includes a sonic generator 300', including a converter 302' an elongate horn 304' enclosed in a housing 200', and a multiple unit dose revolver 600' enclosed in a cap 228. The unit dose revolver 600' is removable from the housing 200' to permit replacement thereof after use. The housing 200' also contains a battery 402' a control board 404' and a control shaft 220 on which a pair of control springs 216*a* and 216*b* are located. These control springs cooperate with a control lever 222 to control movement of the sonic generator 300'. When the control lever 222 is in an upright position (222*a*, in solid line), it bears on the front of the sonic converter 302' and compresses the rear control spring 216*a* holding the horn 304' away from the revolver, permitting a user to rotate a unit dose capsule 602' into position, in alignment with the horn 304' by movement of a knurl 224. When the control lever 222 is in a forward position (222*b* in phantom), the rear control spring 216*a* (which is stronger than the forward control spring 216*b*) urges the horn 304' toward the unit dose capsule 602' aligned therewith to generate an aerosol mist through a window 226 in the cap 228.

In one embodiment shown in FIGS. 14-15, the multiple unit dose revolver 600' comprises a top cover 6002, a reservoir disk 6004 and a membrane 6006 disposed therebetween. These components are arranged and configured for snap-fitting the top cover 6002 to the reservoir disk 6004 using a plurality of inner catches 6008 disposed about a center portion of the top cover 6002 and outer catches 6009 disposed about the periphery of the top cover 6002. The resulting assembly provides a plurality of unit dose capsules 6020 having the features as described above. Inner catches 6008 engage the rim 6010 of a central aperture 2012 of the reservoir disk 6004, and outer catches 6009 engage the outer perimeter 2013 of the reservoir disk 6004. A plurality of knurls 224 is disposed about the outer perimeter of the top cover 6002.

One of ordinary skill in the art will recognize useful materials for these elements. However, a general guidance follows. The top cover 6002 is preferably formed from a material that is less rigid than the reservoir disk 6004. The ultrasonically deformable membrane 6006 is preferably between 25 and 75 microns thick made of a material capable of standing higher temperatures but still deformable while heated (with thermalized ultrasonic energy in this case). The reservoir disk 6004 is preferably formed of a material rigid enough not to dampen the ultrasonic energy through deformation during the misting (while the ultrasonic transducer advances into the cavity deforming the membrane).

Figures 1, 2:
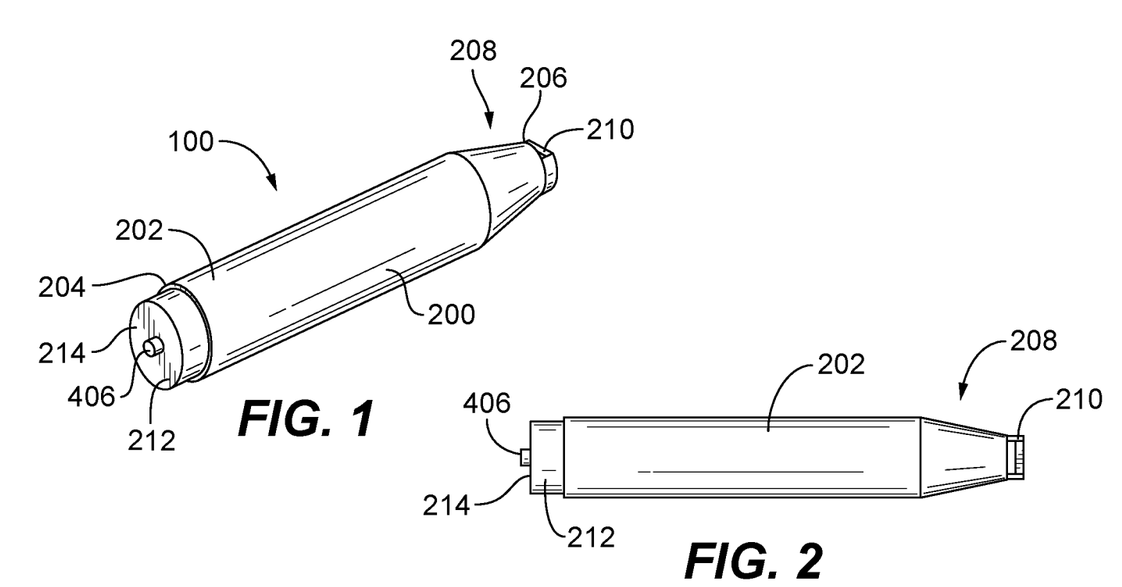
FIG. 1 is a perspective view of a unit dose aerosol misting device according to one embodiment of the present invention.
FIG. 2 is a top plan view of the unit dose aerosol misting device of FIG. 1.
Figures 3, 4:
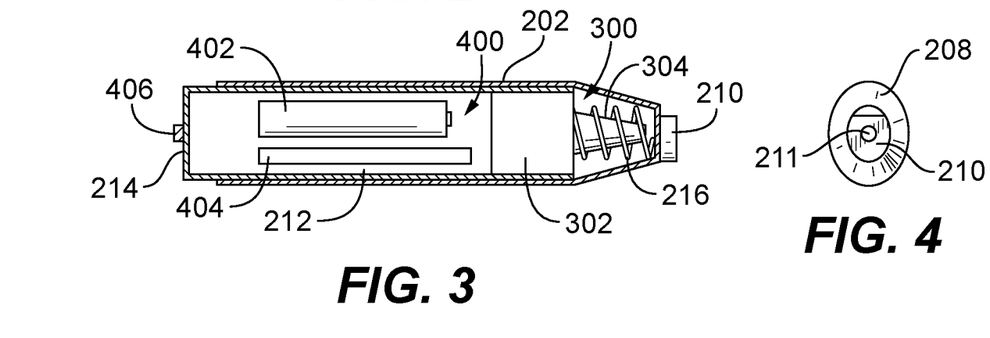
FIG. 3 is a side view of the unit dose aerosol misting device of FIG. 1 with the housing removed to reveal interior elements.
FIG. 4 is an end view of the front, dispensing portion of the unit dose aerosol misting device of FIG. 1.
Figure 5:
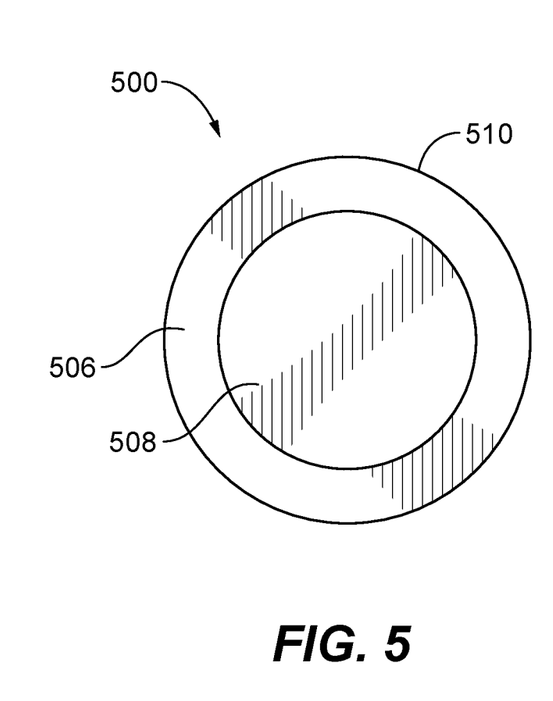
FIG. 5 is a back view of a unit dose capsule useful in the unit dose aerosol misting device of FIG. 1.
Figure 6:
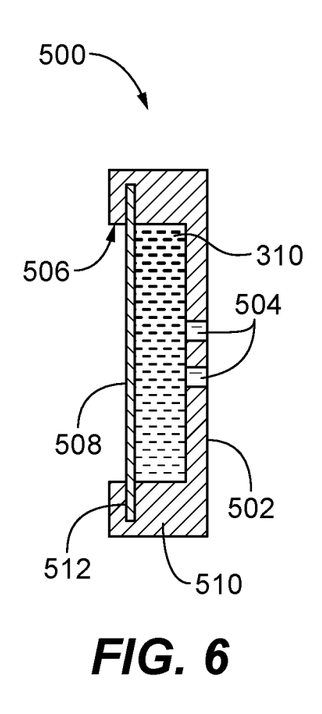
FIG. 6 is a cross-section along line 6-6 of the unit dose capsule of FIG. 5.
Figure 7:
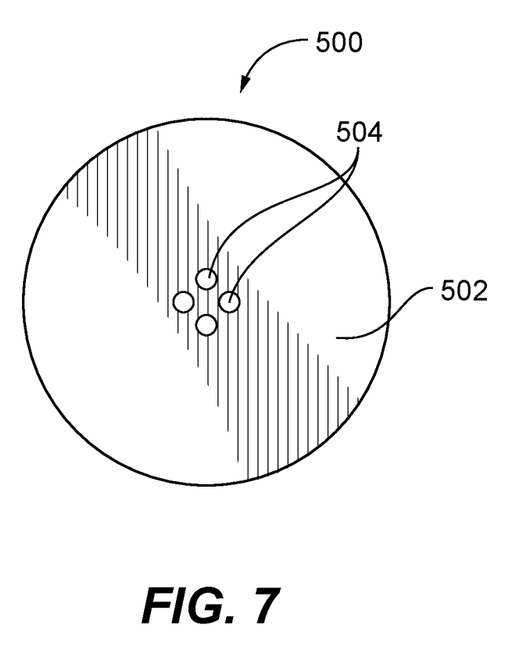
FIG. 7 is a front view of the unit dose capsule of FIG. 5.
Figure 8A:
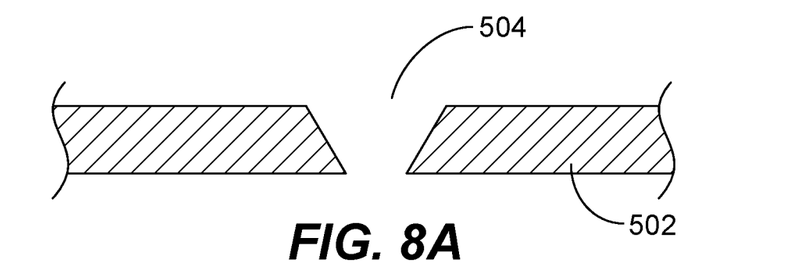
FIGS. 8A-8C are alternative forms of delivery openings in the unit dose capsule of FIG. 5.
Figure 8B:
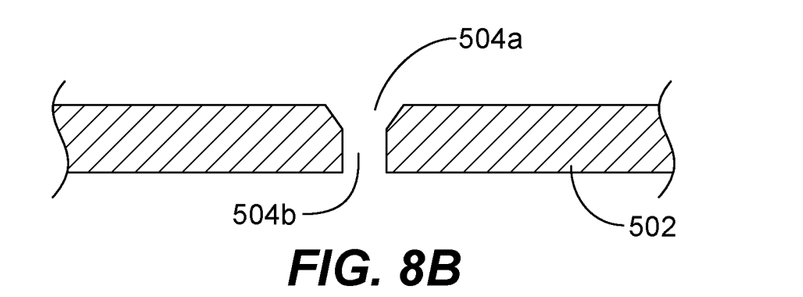
Figure 8C:
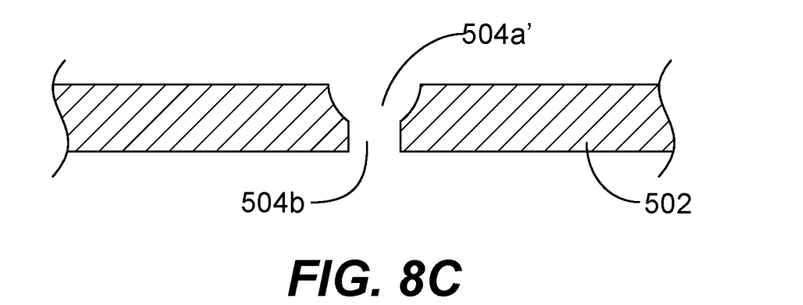
Figure 9:
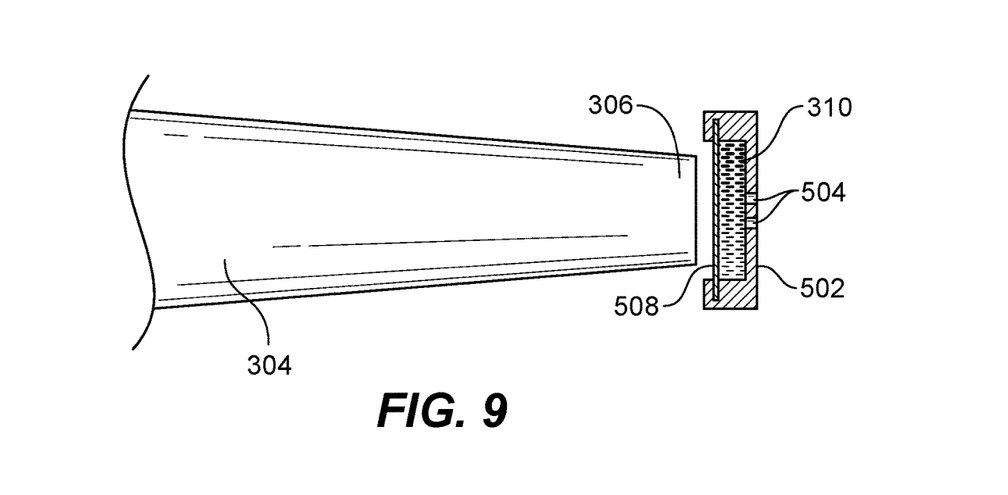
FIG. 9 is an enlarged view of the distal end of the elongate horn prior to engaging the unit dose capsule.
Figure 10:
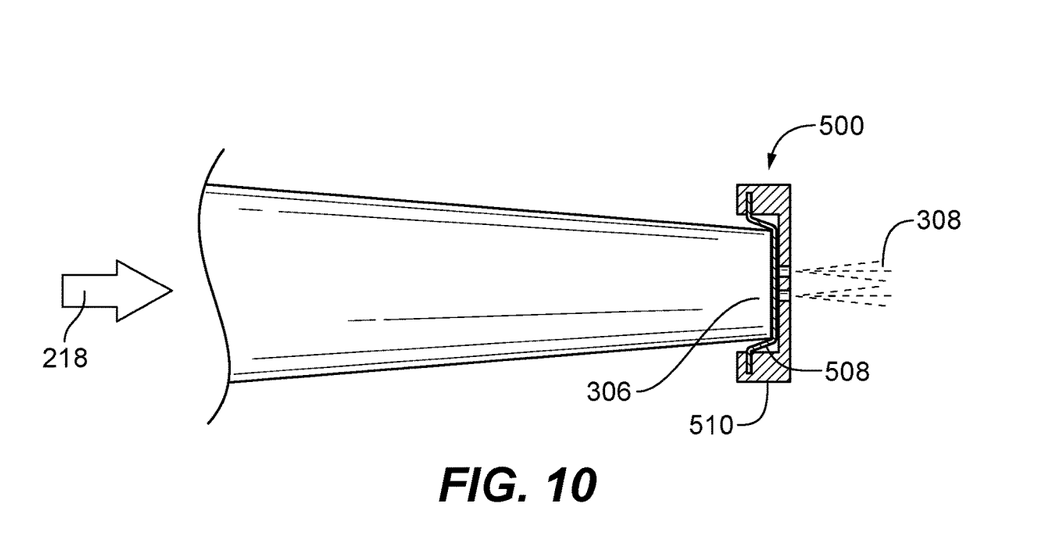
FIG. 10 is an enlarged view of the distal end of the elongate horn while engaged with the unit dose capsule to generate an aerosol mist.
Figure 11A:
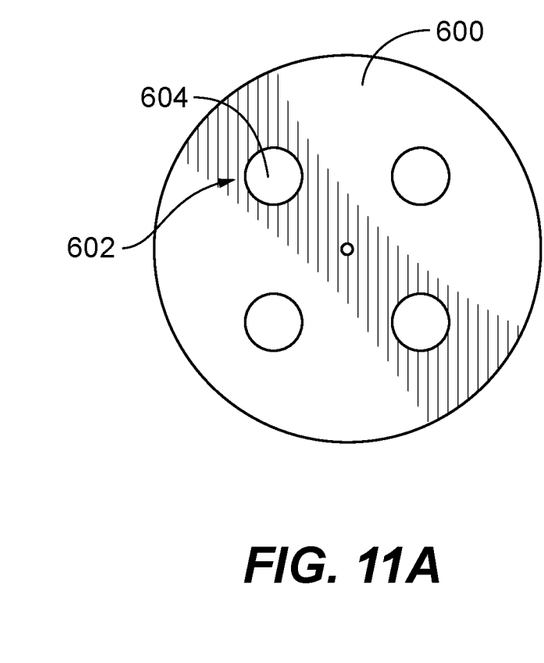
FIG. 11A is a plan view of the horn-engaging side of a multi-unit dose revolver configured for engagement with the horn of a sonic misting device.
Figure 11B:
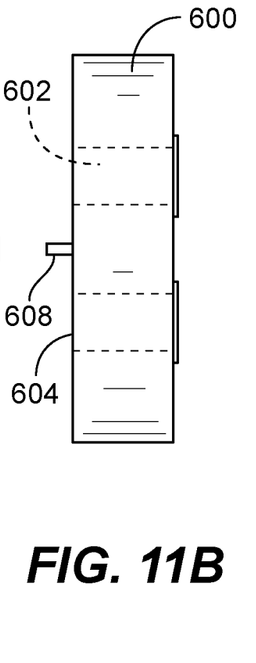
FIG. 11B is a side view of the multi-unit dose revolver of FIG. 11A.
Figure 11C:
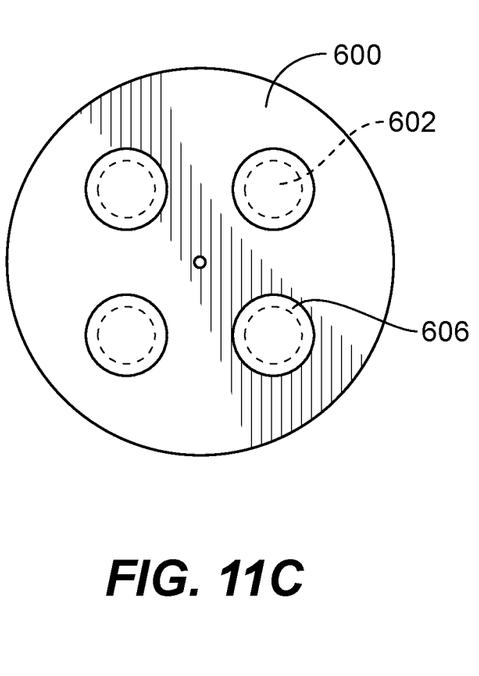
FIG. 11C is a plan view of the opposite, exterior side of the multi-unit dose revolver of FIG. 11A.
Figure 12:
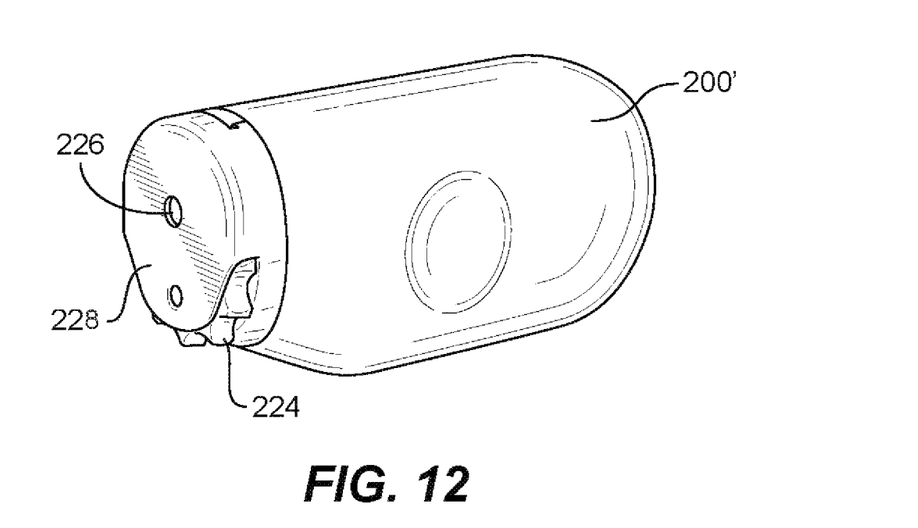
FIG. 12 is a perspective view of a multi-unit dose sonic misting device according to an alternate embodiment of the present invention.
Figure 13:
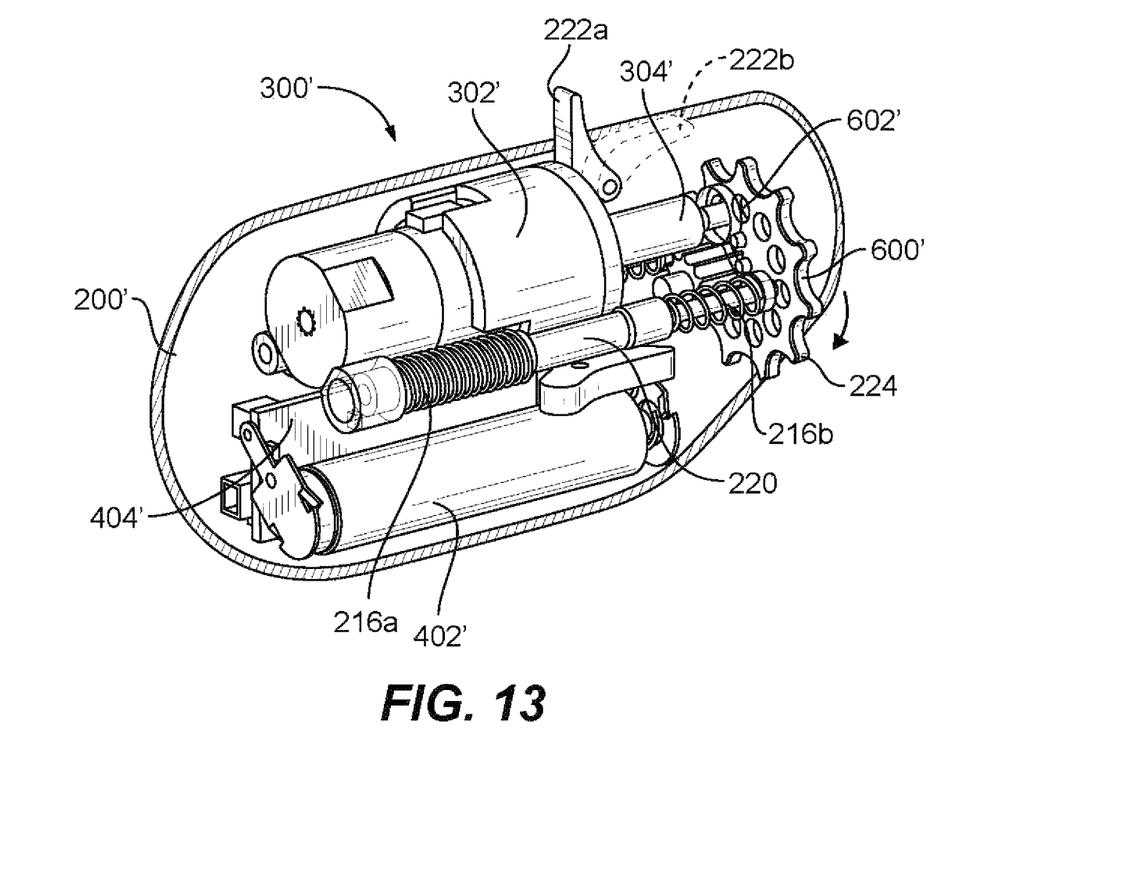
FIG. 13 is a perspective view of the multi-unit dose sonic misting device of FIG. 12 with the housing removed.
Figure 14:
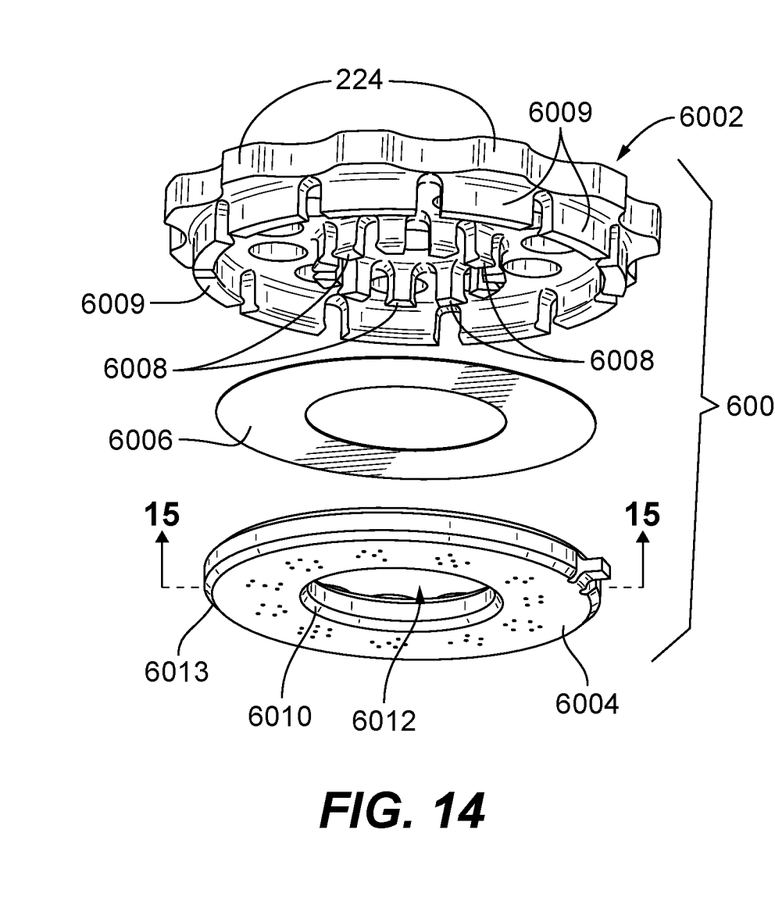
FIG. 14 is an exploded, perspective view of a multiple unit dose revolver, such as shown in FIG. 13.
Figure 15:
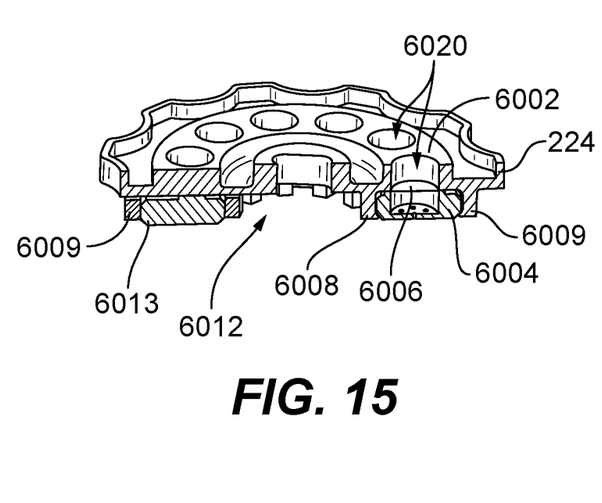
FIG. 15 is a cross-section along line 15-15 of the assembled multiple unit dose revolver of FIG. 14.
Figure 16:
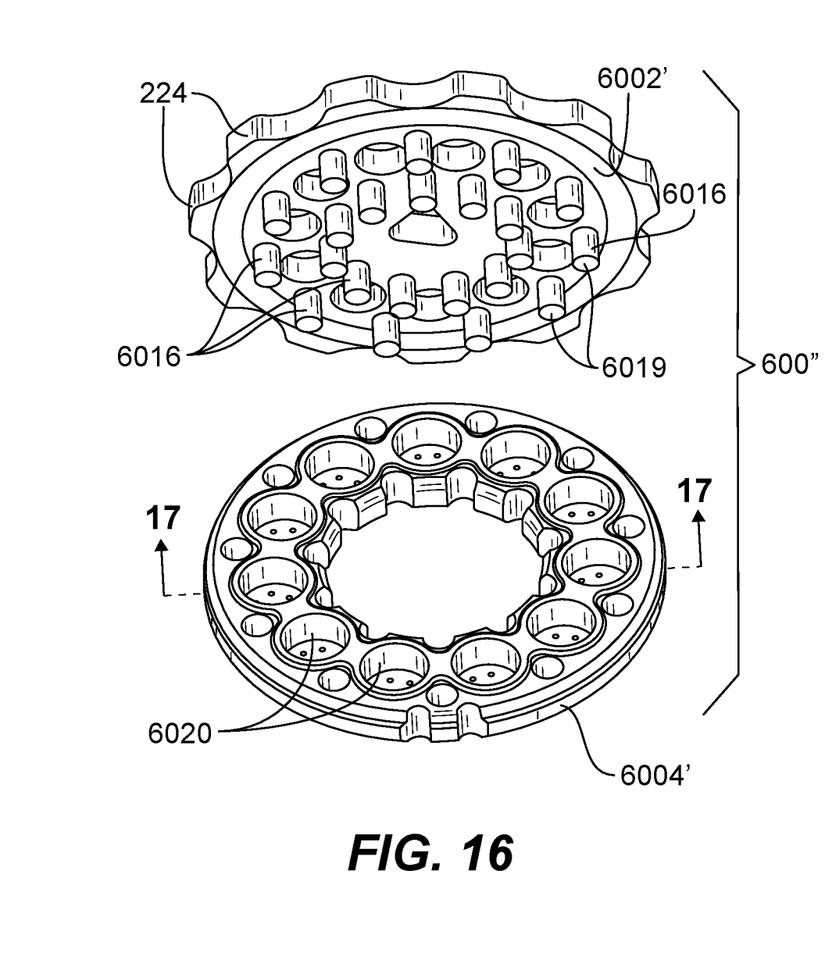
FIG. 16 is an exploded, perspective view of an alternative multiple unit dose revolver, such as shown in FIG. 13.
Figure 17:
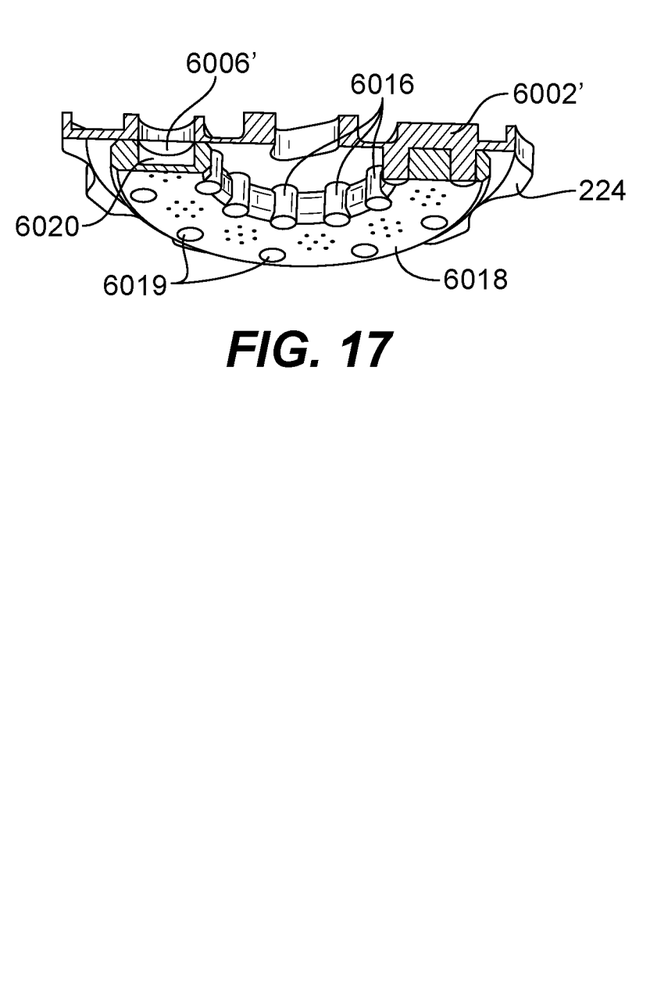
FIG. 17 is a cross-section along line 17-17 of the assembled multiple unit dose revolver of FIG. 16.

In another embodiment shown in FIGS. 16-17, the multiple unit dose revolver 600" comprises a top cover 6002', a reservoir disk 6004' and a membrane 6006' (FIG. 17; similar to that of FIG. 14, but not shown in FIG. 16) disposed therebetween. These components are arranged and configured for ultrasonically welding the top cover 6002' to the reservoir disk 6004' using a plurality of columns 6016 disposed about the top cover 6002'. These columns 6016 are fitted into a plurality of apertures 6014 of the reservoir disk 6004'. These columns 6016 provide an engagement at the bottom surface 6018 of the reservoir disk 6004' to enable ultrasonic or other form of thermal welding (including precision laser welding) or even adhesives, such as UV-cured epoxy between the distal ends 6019 and the bottom surface 6018 of the reservoir disk 6004'. The resulting assembly provides a plurality of unit dose capsules 6020' having the features as described above. A plurality of knurls 224 is disposed about the outer perimeter of the top cover 6002'.

As indicated above, as sonic generators are more expensive than traditional squeeze and spray bottles, it is important to separate the expensive and reusable sonic generator and horns from the relatively inexpensive and potentially disposable liquid reservoirs. One of ordinary skill in the art will recognize the general assembly of the handheld sonic misting device of the present invention. However, the interaction of the following elements is important to consider. First the distal end 306 of the horn 304 and the membrane 508 engage intimately to minimize energy loss due to inefficient motion transfer from the horn to the wall of the nozzle opposite the delivery openings to minimize heat buildup and to maximize control of the resulting aerosol plume. In addition, the distal end 306 of the horn 304 should engage the center of the membrane 508 throughout the operation. In the event that the distal end 306 of the horn 304 and the walls 510 of the reservoir approach too closely, the membrane 508 can be ruptured, thereby permitting the liquid 310 to contaminate the horn 304.

The housing may comprise any suitable material or combination of materials. Preferably, it includes one or more hard, heat-resistant material(s). Examples of suitable materials include, without limitation, metals, alloys, plastics or composite materials containing one or more of those materials, or ceramics. Plastics can include thermoplastics that are suitable for food or pharmaceutical applications, for example, polypropylene, polyether etherketone (PEEK) and polyethylene. Preferably, the material is light and non-brittle. The housing may be fabricated by plastic injection molding, or any other suitable technique, and it is preferably ergonomic and adapted to fit comfortably in a hand of a user. In a preferred embodiment, the housing has a maximum linear dimension (length) of up to about 20 cm, more preferably, up to about 15 cm, and most preferably up to about 10 cm. Preferably, the maximum dimension perpendicular to the length is 8 cm, more preferably, 5 cm.

Again, the electric power and control system 400 includes a power source, such as a battery 402, one or more control boards 404. The power source 402 is sized to provide sufficient power for the sonic generator and any additional control circuitry and/or electromechanical subsystems. For example, the manual operation driving the sonic horn into contact with the unit dose capsule may be replaced by a linear motor for greater control. The power source is preferably replaceable and/or rechargeable and may include devices such as a capacitor or, more preferably, a battery. In a presently preferred embodiment, the power source 402 is a rechargeable battery including, without limitation, lithium-based cells, including lithium polymer batteries. One example of an internal power source is a lithium polymer cell providing a voltage of about 3.7 V that has a capacity of at least about 200 milliamp hours (mAh).

The unit dose capsule 500 (which may also be described as a pod or a cartridge) can be packaged in an air-tight container, such as a metallic foil or plastic pouch or blister pack. Each unit dose capsule will provide sufficient liquid for the desired treatment. For example, for application to a human eye, a capsule may contain about 5 to about 20 microliters (μl); for application to a human nasal cavity, a capsule may contain about 50 to 150 μl; and for an antiseptic wound care product, a capsule may contain more than 200 μl. One of ordinary skill in the art will recognize that these volumes may be modified for these and other desired applications.

The capsule 500 may be formed of several components, such as the walls 510, first surface 502 having the delivery opening(s) 504, and the membrane 508. The walls and first surface are preferably manufactured of rigid plastic. For example, the unit dose capsule can be formed of metal or engineering plastic and machined or molded within appropriate tolerances to fit into the receptacle at the distal end of the elongate horn. A non-limiting list of useful materials include acetal resins (such as available from DuPont® Engineering Polymers under the DELRIN® brand), polyether ether ketones, amorphous thermoplastic polyetherimide (PEI) resins (such as available from SABIC under the ULTEM® brand), polycarbonate resins, polyester resins, and the like.

To provide effective aerosolization, the membrane should be (1) as thin as possible in the 25 to 75 μm thick, (2) manufactured of a high temperature plastic (fluorinated such as PFA), (3) flexible, and (4) susceptible to ultrasonic welding during manufacture. The capsule can be assembled by forming the nozzle surface and side walls from one of the materials listed above and the membrane can be joined thereto by adhesives, thermobonding, ultrasonic welding, clamping the membrane between the side walls and an additional ring which can then be screwed or bolted to the side walls.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of generating an aerosol mist using a handheld device comprising a housing containing a sonic generator comprising a converter and an elongate horn having a proximal end coupled to the converter and a distal end that is arranged and configured to transmit sonic energy outside of the housing, and a power source coupled to the sonic generator; the method comprising the steps of:
   a) coupling a first unit dose capsule to the distal end of the elongate horn, the capsule comprising:
      i) a first portion comprising a deformable membrane adapted to releasably engage the distal end of the elongate horn and transmit sonic energy therethrough;
      ii) a second portion comprising at least one nozzle, wherein when coupled to the distal end of the elongate horn, the second portion is disposed in an outwardly facing orientation; and
      iii) a reservoir containing a liquid composition in communication with the at least one nozzle;
   b) energizing the sonic generator to deliver sonic energy to the first capsule coupled to the distal end of the elongate horn to generate an aerosol mist by forcing the liquid through the at least one nozzle by:
      i) engaging the distal end of the elongate horn with the deformable membrane;
      ii) transmitting sonic energy through the deformable membrane to the liquid composition;
      iii) deforming the deformable membrane by advancing the distal end of the elongate horn into the reservoir as the liquid composition is dispensed to form the aerosol mist;
   c) removing the first unit dose capsule from the distal end of the elongate horn;
   d) coupling a second unit dose capsule to the distal end of the elongate horn; and
   e) energizing the sonic generator to deliver sonic energy to the second unit dose capsule coupled to the distal end of the elongate horn by repeating steps b) i)-b) iii), above.

2. The method of claim 1, wherein the second unit dose capsule is substantially identical to the first unit dose capsule and contains a substantially identical liquid composition.

3. The method of claim 1, wherein the second unit dose capsule is substantially identical to the first unit dose capsule and contains a second liquid composition.

4. The method of claim 1, wherein the first portion of the unit dose capsule is directly engaged with the distal end of the elongate horn.

* * * * *